US011465096B2

(12) United States Patent
Landau et al.

(10) Patent No.: US 11,465,096 B2
(45) Date of Patent: Oct. 11, 2022

(54) TRAP FOR USE WITH GAS SAMPLING DEVICES

(71) Applicant: MDC INDUSTRIES LTD., Sderot (IL)

(72) Inventors: Ruby Landau, Kohav Michael (IL); Haim Yanko, Misgav Dov (IL)

(73) Assignee: MDC INDUSTRIES LTD., Sderot (IL)

( * ) Notice: Subject to any disclaimer, the term of this patent is extended or adjusted under 35 U.S.C. 154(b) by 613 days.

(21) Appl. No.: 16/340,792

(22) PCT Filed: Jan. 8, 2018

(86) PCT No.: PCT/IL2018/050028
§ 371 (c)(1),
(2) Date: Apr. 10, 2019

(87) PCT Pub. No.: WO2018/127925
PCT Pub. Date: Jul. 12, 2018

(65) Prior Publication Data
US 2020/0197862 A1  Jun. 25, 2020

Related U.S. Application Data

(60) Provisional application No. 62/506,176, filed on May 15, 2017, provisional application No. 62/443,888, filed on Jan. 9, 2017.

(51) Int. Cl.
| | |
|---|---|
| *B01D 53/26* | (2006.01) |
| *A61B 5/083* | (2006.01) |
| *A61B 5/097* | (2006.01) |

(52) U.S. Cl.
CPC .......... *B01D 53/268* (2013.01); *A61B 5/0836* (2013.01); *A61B 5/097* (2013.01); *A61B 2562/12* (2013.01)

(58) Field of Classification Search
None
See application file for complete search history.

(56) References Cited

U.S. PATENT DOCUMENTS

| 4,886,528 A | 12/1989 | Aaltonen et al. |
| 5,368,021 A | 11/1994 | Beard et al. |

(Continued)

FOREIGN PATENT DOCUMENTS

| DE | 10014829 B4 | 4/2006 |
| GB | 2224957 A | 5/1990 |
| WO | 2014045182 A1 | 3/2014 |

OTHER PUBLICATIONS

International Search Report and Written Opinion from International Application No. PCT/IL2018/050028 dated Mar. 21, 2018.

(Continued)

*Primary Examiner* — Jay B Shah
(74) *Attorney, Agent, or Firm* — Dorsey & Whitney LLP (57) ABSTRACT

Apparatus and methods are described, including a water trap (28) that includes an inlet portion (40), via which a mixture of gas and water is configured to enter the water trap, and an outlet portion (42), via which the gas is configured to exit the water trap, the inlet portion and the outlet portion being formed separately from one another and being coupled to one another, such as to form a tube (44) that defines a longitudinal axis and that defines an internal hollow volume through which the gas is configured to flow. A membrane filter (46) is disposed in a flat configuration within the tube, between the inlet portion and the outlet portion, such that the membrane filter is substantially parallel to the longitudinal axis of the tube, the membrane filter being configured to prevent the water from passing therethrough. Other applications are also described.

19 Claims, 7 Drawing Sheets

(56) References Cited

U.S. PATENT DOCUMENTS

| | | | |
|---|---|---|---|
| 5,573,280 A | 11/1996 | Salter et al. | |
| 6,596,167 B2 | 7/2003 | Ji et al. | |
| 6,779,522 B2 | 8/2004 | Smith et al. | |
| 6,783,573 B2 | 8/2004 | Richardson | |
| 7,353,689 B2 | 4/2008 | Weckstroem | |
| 8,240,187 B2 | 8/2012 | Colman et al. | |
| 2009/0020124 A1 | 1/2009 | Roth et al. | |
| 2009/0312662 A1 | 12/2009 | Colman et al. | |
| 2010/0307341 A1 | 12/2010 | Peter et al. | |
| 2011/0237969 A1 | 9/2011 | Eckerbom et al. | |
| 2011/0283884 A1* | 11/2011 | Larsen | A61M 16/1065 96/417 |
| 2014/0180157 A1 | 6/2014 | Levitsky et al. | |
| 2015/0223728 A1 | 8/2015 | Fudge et al. | |

OTHER PUBLICATIONS

U.S. Appl. No. 62/443,888, filed Jan. 9, 2017.
U.S. Appl. No. 62/506,176, filed May 15, 2017.
"Trouble-free sidestream gas analysis", Nomoline™, 2009, pp. 1-8.

* cited by examiner

TRAP FOR USE WITH GAS SAMPLING DEVICES

CROSS-REFERENCE TO RELATED APPLICATIONS

The present application is a US national phase application of PCT Application No. PCT/IL/2018/050028 to Landau (published as WO 18/127925), filed Jan. 8, 2018, which claims priority from:

U.S. Provisional Application 62/443,888 to Landau, entitled "Trap for use with gas sampling device," filed Jan. 9, 2017; and U.S. Provisional Application 62/506,176 to Landau, entitled "Trap for use with gas sampling device," filed May 15, 2017.

Both of the above-referenced applications are incorporated herein by reference.

FIELD OF EMBODIMENTS OF THE INVENTION

Some applications of the present invention generally relate to medical apparatus and methods. Specifically, some applications of the present invention relate to apparatus and methods for use with a capnometer.

BACKGROUND

Capnography is used to measure the partial pressure of carbon dioxide in inhaled and/or exhaled respiratory gases. Capnometer sensing chambers typically operate by transmitting infrared light through a sample of the respiratory gases, and measuring absorption of the infrared light by the sample. The level of absorption of the infrared light is indicative of the partial pressure of the carbon dioxide within the sample.

Capnometers are classified as either non-diverting, or diverting. Non-diverting capnometers, which are also known as mainstream capnometers, measure the partial pressure of the carbon dioxide by performing infrared light absorption sensing at an airway of the subject. Diverting capnometers, which are also known as sidestream capnometers, divert the respiratory gases to a remote sensing chamber via tubing. Typically, while passing through the tubing, there is some condensation of water vapor that is present in the respiratory gases. The condensed water may damage the sensing chamber, and/or may interfere with the measurements that are performed by the sensing chamber. Therefore, typically the respiratory gases pass through a water trap before being analyzed within the sensing chamber. The water trap is configured to trap any condensed water and to prevent the condensed water from entering the sensing chamber.

The response time of a capnometer depends upon parameters known as transit time and the rise time. The transit time is the time required for the sample to move from the point at which the sample is sampled (e.g., a mask or cannula at the subject's mouth or nose) to the sensing chamber. The rise time is typically defined as the time taken by the output from the capnometer to change from 10 percent of the final value to 90 percent of the final value, in response to a step change in the pressure of the carbon dioxide, in which case the rise time is referred to as "T90 rise time." (In some cases, rise time is defined as the time taken by the output from the capnometer to change from 10 percent of the final value to 70 percent of the final value, in which case the rise time is referred to as "T70 rise time.") The value of the rise time of a capnometer dictates how "crisp" (i.e., how straight and unblurred) the waveforms of the capnometer will be. The rise time is lengthened by interference to the flow of respiratory gases due to friction along the tubing and filters, for example. Such interference is particularly pertinent when diverting capnometers are used at a relatively low gas flow rate (e.g., a flow rate of approximately 50 ml/min. or less.) Rise time is an indicator of the system resolution (i.e., separation between breaths) and the system accuracy.

SUMMARY OF EMBODIMENTS

There is provided, in accordance with some applications of the present invention, a water trap including an inlet portion, via which fluid (e.g., a mixture of liquid and gas) enters the water trap, and an outlet portion, via which fluid (e.g., gas) exits the water trap. The inlet portion and the outlet portion are formed separately from one another, and are coupled to one another, such as to form a tube that defines a longitudinal axis. A membrane filter is disposed in a flat configuration within the tube, between the inlet portion and the outlet portion, such that the membrane filter is substantially parallel to the longitudinal axis of the tube.

Due to the membrane filter being disposed in the aforementioned configuration, the membrane filter is disposed such that it is substantially parallel (e.g., parallel) to the direction of fluid flow through the water trap. Thus, the water trap is configured such that respiratory gases that pass through the water trap typically pass from the inlet portion to the outlet portion, via the filter, without the direction of fluid flow of the gases substantially changing. In this manner, laminar flow of the respiratory gases is substantially maintained, as the respiratory gases pass through the water trap. Furthermore, since the filter is disposed between the inlet portion and the outlet portion along the length of the internal hollow volume through which respiratory gases flow, even if some water becomes trapped on a portion of the membrane filter on the inlet side of the water trap, the respiratory gases are typically able to pass through other portions of the membrane filter. Further typically, since the filter is disposed between the inlet portion and the outlet portion along the length of the internal hollow volume through which the respiratory gases flow, the respiratory gases pass through the filter along substantially the full length of the internal hollow volume, which typically minimizes dead space within the internal hollow volume and reduces turbulence relative to if there was more dead space within the internal hollow volume. For some applications, by being in the above-described manner, the water trap (1) provides a relatively low pressure drop (i.e., the difference between the pressure of the gas (a) at the inlet and outlet ports and (b) inside the water trap), and (2) additionally provides a relatively low rise time, as described in further detail hereinbelow.

There is therefore provided, in accordance with some applications of the present invention, apparatus including:

a water trap comprising:

an inlet portion, via which a mixture of gas and water is configured to enter the water trap;

an outlet portion, via which the gas is configured to exit the water trap, the inlet portion and the outlet portion being formed separately from one another and being coupled to one another, such as to form a tube that defines a longitudinal axis and that defines an internal hollow volume through which the gas is configured to flow; and a membrane filter disposed in a flat configuration within the tube, between the inlet portion and the outlet portion, such that the membrane filter is substantially parallel to the longitudinal axis of the tube, the membrane filter being configured to prevent the water from passing therethrough.

In some applications, the water trap is configured to retain the water that is prevented from passing through the membrane filter within the inlet portion.

In some applications, the water trap does not include a reservoir into which to transfer water that is prevented from passing through the membrane filter.

In some applications, the water trap does not include a channel via which to transfer water that is prevented from passing through the membrane filter out of the inlet portion.

In some applications, the water trap is configured to be used with a capnometer that includes a sensing chamber, and the water trap is configured to prevent water from entering the sensing chamber.

In some applications, a length of the internal hollow volume defined by the tube formed by the inlet portion and the outlet portion is between 30 mm and 150 mm.

In some applications, a length of the internal hollow volume defined by the tube formed by the inlet portion and the outlet portion is between 20 mm and 50 mm.

In some applications, a volume of the internal hollow volume defined by the tube formed by the inlet portion and the outlet portion is between 0.05 cc and 0.3 cc.

In some applications, a volume of the internal hollow volume defined by the tube formed by the inlet portion and the outlet portion is between 0.02 cc and 0.04 cc.

In some applications, a ratio between an internal hollow volume defined by the inlet portion and an internal hollow volume defined by the outlet portion is between 2:1 and 4:1.

In some applications, a ratio between an internal hollow volume defined by the inlet portion and an internal hollow volume defined by the outlet portion is between 1:1 and 2:1.

In some applications, the water trap is configured such that a T90 rise time of respiratory gases through the water trap at a flow of 50 cc/min is less than 200 ms, when the water trap is in a standalone configuration.

In some applications, the membrane filter, by being disposed substantially parallel to the longitudinal axis of the tube defined by the inlet and outlet portions, is configured to be substantially parallel to a direction of fluid flow through the water trap.

In some applications, the membrane filter, by being disposed substantially parallel to the longitudinal axis of the tube defined by the inlet and outlet portions, is configured such that gas passes from the inlet portion to the outlet portion, via the membrane filter, without a direction of flow of the gas substantially changing.

In some applications, the membrane filter, by being disposed substantially parallel to the longitudinal axis of the tube defined by the inlet and outlet portions, is configured to substantially maintain laminar flow of gas that passes through the water trap.

In some applications, the water trap is configured such that a pressure drop of gas that passes through the water trap at a flow of 50 cc/min is less than 20 mBar.

In some applications, the membrane filter includes a polymer selected from the group consisting of: expanded polytetrafluoroethylene (EPTFE), polytetrafluoroethylene (PTFE), a polyolefin, glass micro-fiber, polyethersulfone (PES), polypropylene (PP), and polyvinylidene fluoride (PVDF).

In some applications, the membrane filter includes a membrane filter having a pore size of between 0.1 microns and 10 microns.

In some applications, the outlet portion is shaped to define one or more internal protruding portions that protrude from an inner surface of the outlet portion.

In some applications, the one or more internal protruding portions that protrude from the inner surface of the outlet portion maintain the membrane filter parallel to the longitudinal axis of the tube defined by the inlet and outlet portions.

There is further provided, in accordance with some applications of the present invention, a method including:
manufacturing a water trap by:
providing an inlet portion;
providing an outlet portion;
placing a membrane filter in a flat configuration between the inlet portion and the outlet portion, the membrane filter being configured to prevent water from passing therethrough; and
while the membrane filter is disposed between the inlet portion and the outlet portion coupling the inlet portion and the outlet portion to one another, such that inlet portion and the outlet portion define a tube that defines a longitudinal axis and that defines an internal hollow volume, and the membrane filter is disposed substantially parallel to a longitudinal axis of the tube.

There is further provided, in accordance with some applications of the present invention, a method for use with a sensing unit of a capnometer, the method including:
providing a water trap that includes:
an inlet portion and an outlet portion, the inlet portion and the outlet portion being coupled to one another, such as to form a tube that define a longitudinal axis and that defines an internal hollow volume, and
a membrane filter disposed in a flat configuration within the tube, between the inlet portion and the outlet portion, such that the membrane filter is substantially parallel to the longitudinal axis of the tube; and
placing the water trap in fluid communication with respiratory gases and water exhaled by a subject, and the sensing unit of the capnometer such that:
the respiratory gases and water enter the water trap via the inlet portion,
the water trap prevents water from entering the sensing unit of the capnometer, by the membrane filter preventing the water from passing therethrough, and
the respiratory gases flow through the membrane filter and out of the outlet portion to the sensing unit of the capnometer.

The present invention will be more fully understood from the following detailed description of embodiments thereof, taken together with the drawings, in which:

DETAILED DESCRIPTION OF EMBODIMENTS

Figure 1:
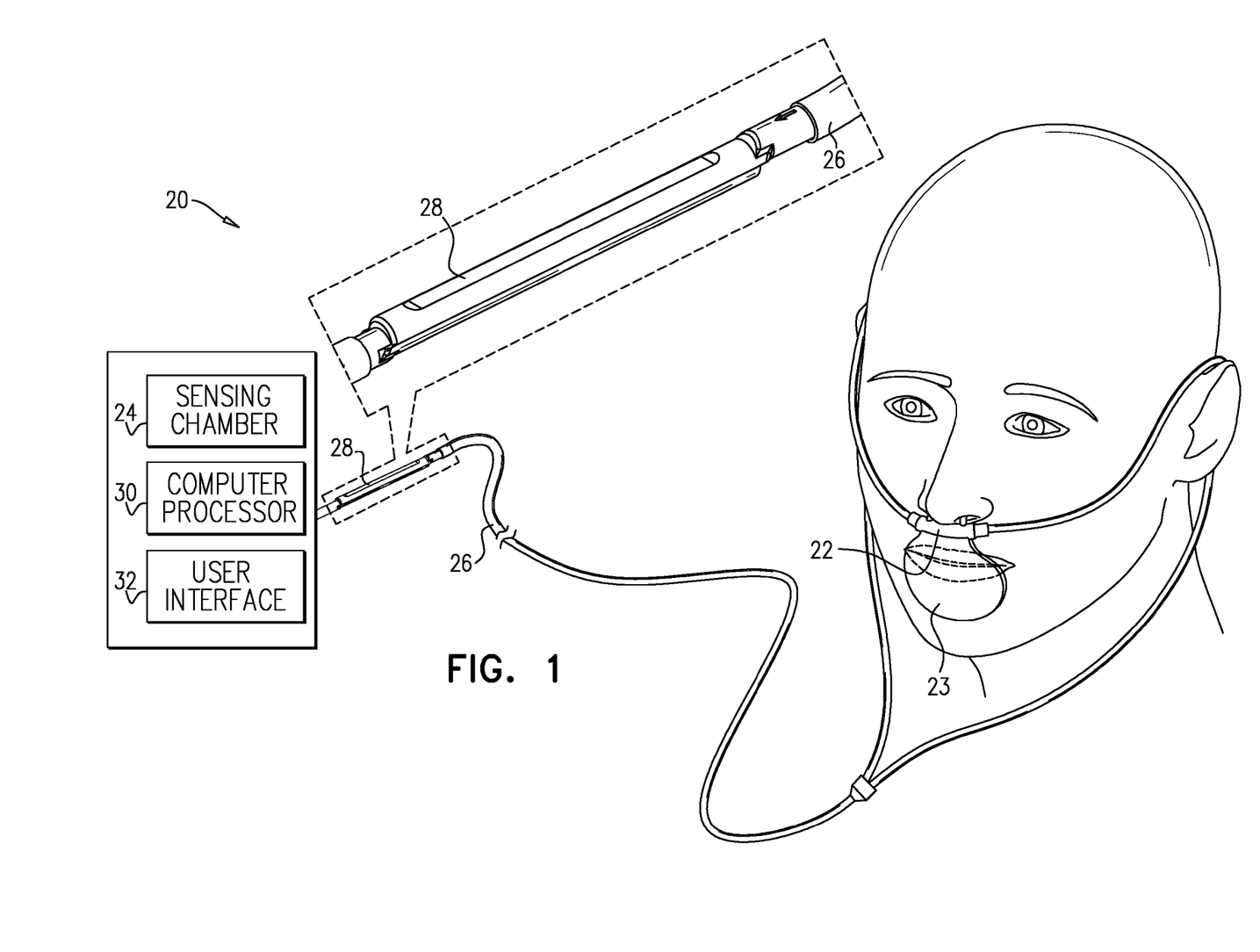
FIG. 1 is a schematic illustration of a capnometer, in accordance with some applications of the present invention.

Reference is now made to FIG. 1, which is a schematic illustration of a capnometer 20, in accordance with some applications of the present invention. For some applications, the capnometer includes a nasal cannula 22, as shown. Alternatively, the capnometer may include an oral cannula 23, and/or a mask. Capnometer as shown in FIG. 1 is a diverting capnometer (also known as a sidestream capnometer), respiratory gases of a subject (such as, carbon dioxide, nitrogen dioxide, and/or anesthetic gases) being diverted to a remote sensing chamber 24 via tubing 26. A water trap 28 is typically disposed between the remote sensing chamber and tubing 26. The water trap is configured to trap any condensed water within the respiratory gases and to prevent the condensed water from entering the sensing chamber.

Typically, the sensing chamber communicates with a computer processor 30, which is configured to analyze data generated by the sensing chamber. Computer processor 30 is typically a hardware device programmed with computer program instructions to produce a special purpose computer. Typically, the operations that are performed by the computer processor transform the physical state of a memory, which is a real physical article, to have a different magnetic polarity, electrical charge, or the like depending on the technology of the memory that is used.

Typically, the computer processor receives instructions from a user, and/or generates outputs to the user, via a user interface 32. For some applications, the user interface includes an input device, such as a keyboard, a mouse, a joystick, a touchscreen device (such as a smartphone or a tablet computer), a touchpad, a trackball, a voice-command interface, and/or other types of input device that are known in the art. For some applications, the user interface includes an output device. Typically, the output device includes a display, such as a monitor. For some applications, the processor generates an output on a computer-readable medium (e.g., a non-transitory computer-readable medium), such as a disk, or a portable USB drive.

Figure 2A:
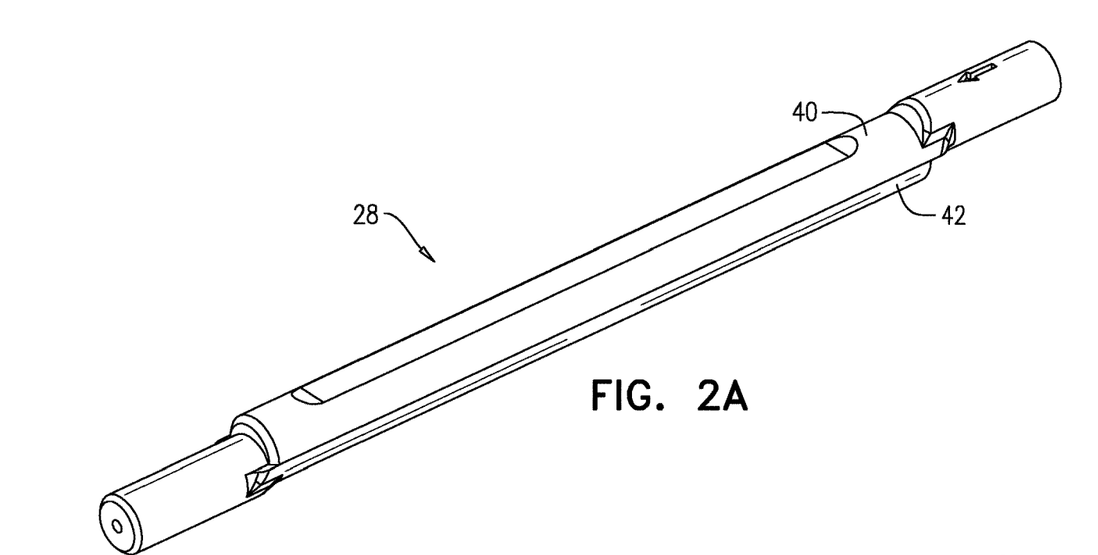
FIGS. 2A and 2B are schematic illustrations of, respectively, a three-dimensional view and a cross-sectional view of a water trap, in accordance with some applications of the present invention.
Figure 2B:
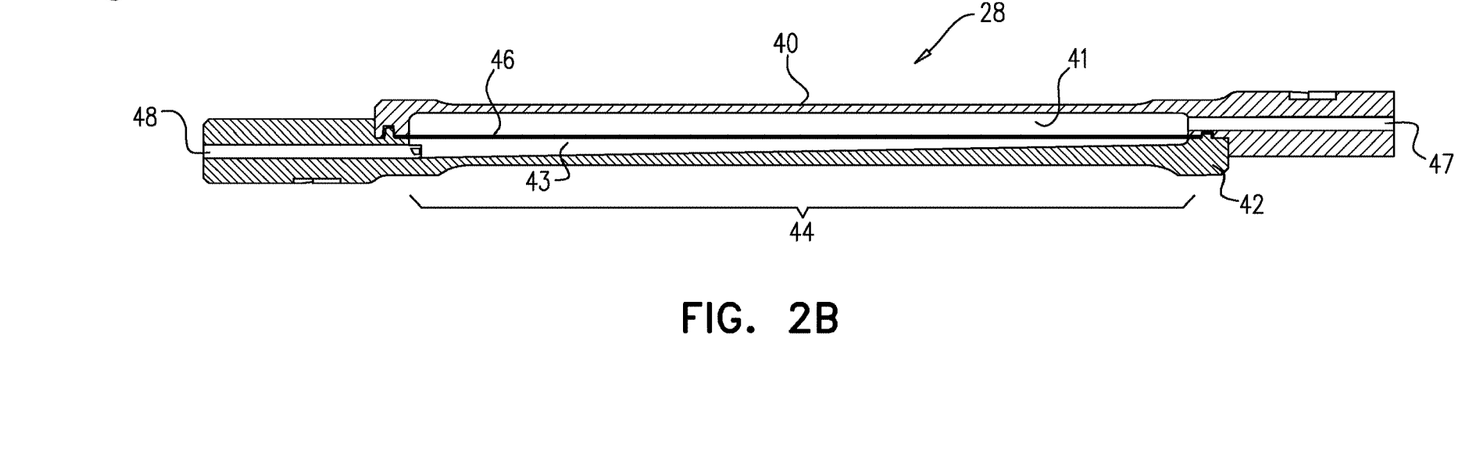

Reference is now made to FIGS. 2A and 2B, which are schematic illustrations of, respectively, a three-dimensional view and a cross-sectional view of water trap 28, in accordance with some applications of the present invention. For some applications, the water trap includes an inlet portion 40 that is configured to receive respiratory gases of the subject from tubing 26. In addition, the water trap includes an outlet portion 42, via which the respiratory gases flow from the water trap into the sensing chamber, in the absence of any condensed water. The inlet portion typically defines an inlet hole 47 via which respiratory gases flow into the water trap, and the outlet portion defines an outlet hole 48, via which respiratory gases flow out of the water trap. For some applications, the diameters of the inlet hole and the outlet hole are equal to each other.

As shown, inlet portion 40 and outlet portion 42 are typically coupled to one another, such as to form a tube 44 that defines a longitudinal axis. The tube typically defines an internal hollow volume (defined by an internal hollow volume 41 defined by the inlet portion and an internal hollow volume 43 defined by the outlet portion) through which respiratory gases flow. A membrane filter 46 is disposed in a flat configuration within the tube, between the inlet portion and the outlet portion (e.g., between the internal hollow volume defined by the inlet portion and the internal hollow volume defined by the outlet portion), such that the membrane filter is parallel to the longitudinal axis of the tube, or is substantially parallel to the longitudinal axis of the tube (e.g., such that a plane defined by the membrane filter is disposed within 10 degrees of being parallel to the longitudinal axis of the tube).

Due to the membrane filter being disposed in the aforementioned configuration, the membrane filter is disposed such that it is substantially parallel (e.g., parallel) to the direction of fluid flow through the water trap. Thus, the water trap is configured such that respiratory gases that pass through the water trap typically pass from the inlet portion to the outlet portion, via the filter, without the direction of fluid flow of the gases substantially changing. In this manner, laminar flow of the respiratory gases is substantially maintained, as the respiratory gases pass through the water trap. Furthermore, since the filter is disposed between the inlet portion and the outlet portion along the length of the internal hollow volume through which respiratory gases flow, even if some water becomes trapped on a portion of the membrane filter on the inlet side of the water trap, the respiratory gases are typically able to pass through other portions of the membrane filter. Further typically, since the filter is disposed between the inlet portion and the outlet portion along the length of the internal hollow volume through which the respiratory gases flow, the respiratory gases pass through the filter along substantially the full length of the internal hollow volume, which typically minimizes dead space within the internal hollow volume and reduces turbulence relative to if there was more dead space within the internal hollow volume.

For some applications, by virtue of the above-described characteristics, water trap 28 has a T90 rise time of less than 200 ms (e.g., less than 160 ms, or less than 120 ms), when the water trap is in a standalone configuration, and used with a gas having a flow rate of 50 cc/min, as evidenced by experiments conducted by the inventors of the present application. It is further noted that, due to configuration of membrane filter 46 being standardized, the rise time of any given unit of the water trap may typically be assumed to the same as other units having similar dimensions. For some applications, when the water trap is placed at the end of tubing having a length of 4 m, and used with a gas having a flow rate of 50 cc/min, the overall T90 rise time of the tubing and the water trap is less than 300 ms (e.g., less than 270 ms), also as evidenced by experiments conducted by the inventors of the present application. (It is noted that, in practice, the water trap is used with gases that pass through the trap at flow rates other than 50 cc/min, and that the aforementioned characteristics are mentioned by way of example.) In addition, the pressure drop of gas that passed through the water trap at a flow of 50 cc/min (i.e., the difference between the pressure of the gas (a) at the inlet and outlet ports and (b) inside the water trap) was found to be less than 20 mBar (e.g., less than 15 mBar), in experiments conducted by the inventors of the present application. Furthermore, even with 0.1 cc of water within the inlet portion of the water trap, the pressure drop of gas that passed through the water trap at a flow of 50 cc/min was found to be less than 60 mBar, in experiments conducted by the inventors of the present application. Typically, by virtue of having a relatively low pressure drop, the flow through the water trap is higher than if the pressure drop of the water trap were to be greater.

Typically, water trap 28 is configured to retain the water that is prevented from passing through the membrane filter within inlet portion 40 of the water trap. Therefore, the water trap typically does not include a reservoir into which to transfer water that is prevented from passing through the membrane filter, and/or the water trap typically does not include a channel via which to transfer water that is prevented from passing through the membrane filter out of the inlet portion. For some applications, the membrane filter, and/or a portion of the inlet portion of the water trap is configured to remove the filtered water from the inlet portion and to release it into the surrounding air, e.g., in response to vapor pressure within the inlet portion exceeding the vapor pressure of the surrounding air. For example, Nafion® tubing may be used, and techniques as described in U.S. Pat. No. 6,779,522 to Smith may be implemented.

Membrane filter 46 typically includes a polymer, such as expanded polytetrafluoroethylene (EPTFE), polytetrafluoroethylene (PTFE), a polyolefin, glass micro-fiber, polyethersulfone (PES), polypropylene (PP), and/or polyvinylidene fluoride (PVDF). For some applications, the membrane filter has a pore size of more than 0.1 microns (e.g., more than 0.5 microns), and/or less than 10 microns (e.g., less than 2 microns), e.g., 0.1-10 microns or 0.5-2 microns.

Figure 3A:
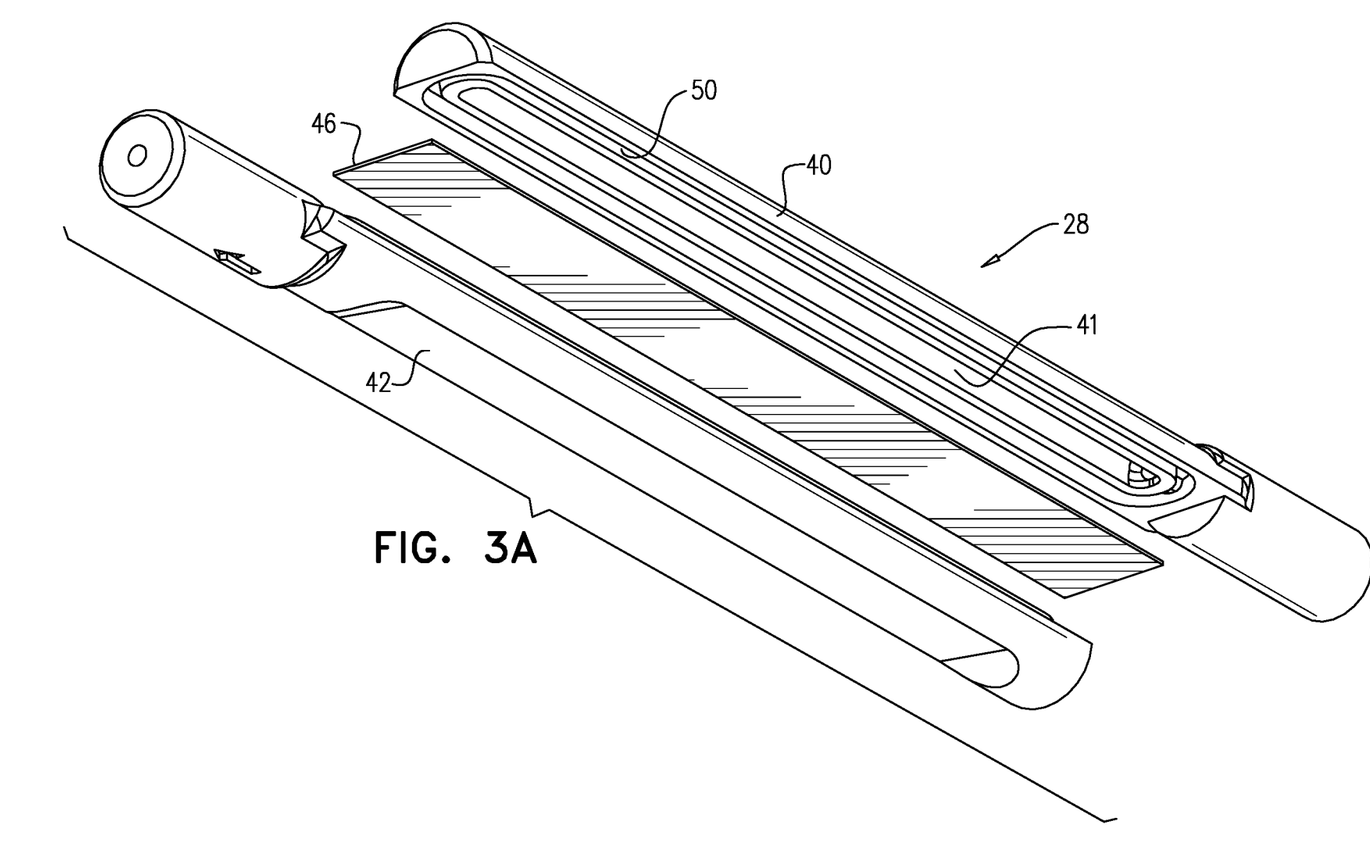
FIGS. 3A and 3B are schematic illustrations of respective exploded views of the water trap, in accordance with some applications of the present invention.
Figure 3B:
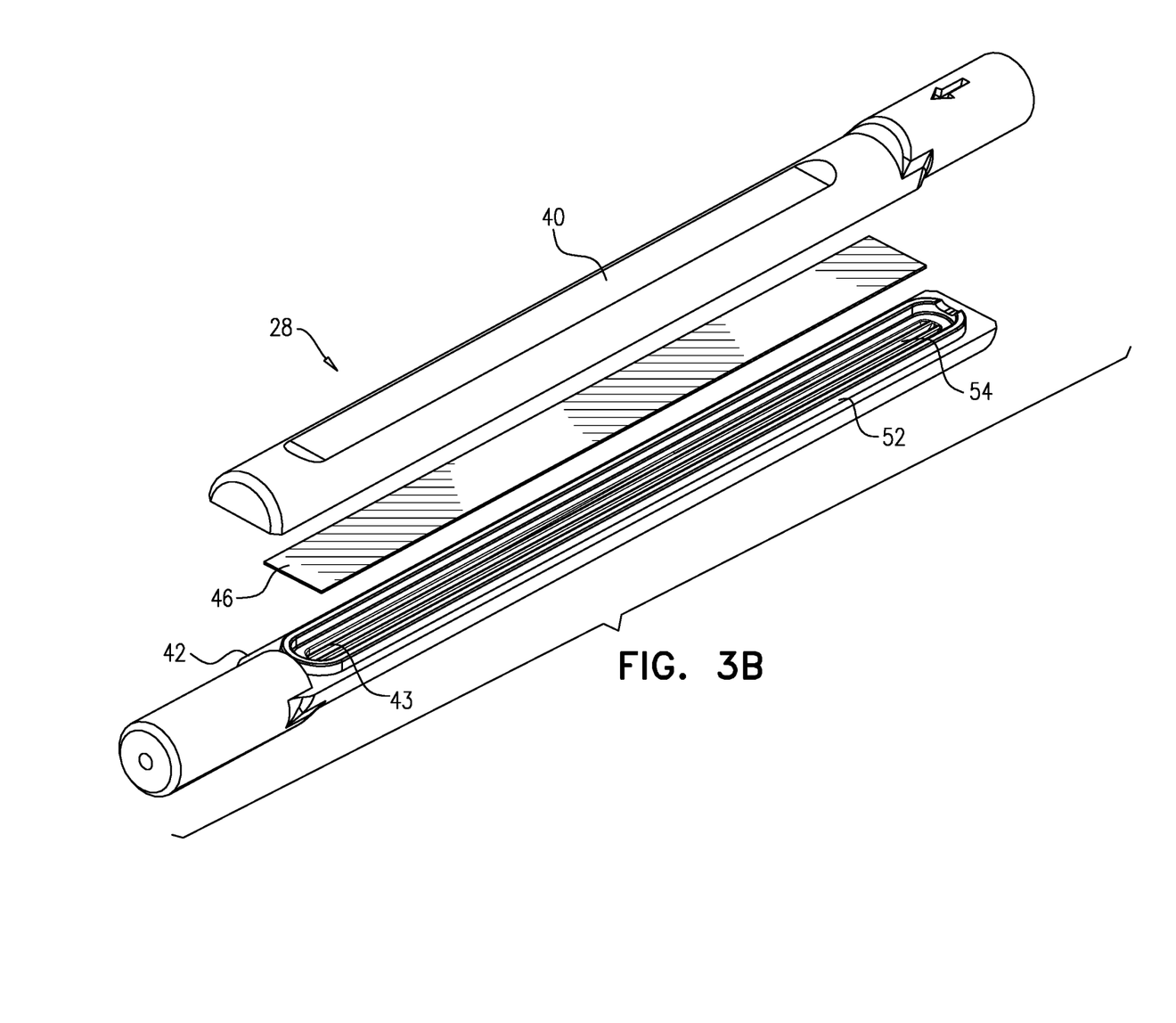

Reference is now made to FIGS. 3A and 3B, which are schematic illustrations of respective exploded views of water trap 28, in accordance with some applications of the present invention.

As shown in FIG. 3A, for some applications, inlet portion 40 is shaped to define engagement portion 50. As shown in FIG. 3B, for some applications, outlet portion 42 is shaped to define engagement portion 52. Typically, engagement portions 50 and 52 are corresponding male and female engagement portions, as shown. For some applications, water trap 28 is manufactured by placing membrane filter 46 between the inlet and outlet portions, before coupling the inlet and outlet portions to one another via engagement portions 50 and 52. Typically, subsequent to coupling the inlet and outlet portions to one another via engagement portions 50 and 52, the inlet and outlet portions are adhered to one another via a heating process, e.g., ultrasonic welding, solvents, and/or heating. For some applications, water trap 28 is manufactured in an automated manner, in an automatic assembly process (e.g., using machinery, and/or robots), using the above-described technique.

As shown in FIG. 3B, for some applications, outlet portion defines one or more internal protruding portions 54, which may be shaped in a grid, or as a grill (i.e., in a plurality of parallel lines), as shown. The protruding portions are configured, by supporting the membrane filter, to maintain the membrane filter parallel to the longitudinal axis of the tube defined by the inlet and outlet portions. For some applications, the protruding portions are arranged a grill (i.e., in a plurality of parallel lines) lines of the grill being parallel to the longitudinal axis of the water trap. For some applications, the protruding portions are configured to direct the respiratory gases toward the outlet hole of the outlet portion.

Typically, the internal hollow volume of the outlet portion is less than that of the inlet portion, since, unlike the inlet portion, the outlet portion is not configured to house filtered condensed water. For some applications, the ratio between the internal hollow volume of the inlet portion (i.e., the volume of internal hollow volume 41 defined by the inlet portion) and the internal hollow volume of the outlet portion (i.e., the volume of internal hollow volume 43 defined by the outlet portion) is between 2:1 and 4:1. For some applications, the internal protruding portions are configured to occupy some of the internal hollow volume of the outlet portion, such that the internal hollow volume of the outlet portion is at a desirable level, relative to the internal hollow volume of the inlet portion.

Typically, the inlet and outlet portions of water trap 28 are shaped such that the length of the internal hollow volume defined by the tube through which the respiratory gases flow is more than 30 mm, and/or less than 150 mm, e.g., between 30 mm and 150 mm. For some applications, the diameter of the internal hollow volume defined by the tube through which the respiratory gases flow is more than 1 mm, and/or less than 4 mm, e.g., between 1 mm and 4 mm. Typically, the volume of the internal hollow volume defined by the tube through which the respiratory gases flow is more than 0.05 cc and/or less than 0.3 cc, e.g., between 0.05 cc and 0.3 cc. For some applications, the internal hollow volume defined by the inlet portion is more than 0.1 cc, e.g., approximately 0.15 cc (e.g., 0.15 cc plus/minus 2 cc).

It is noted that the water trap typically has dimensions as described in the above paragraph, for cases in which the water trap is configured for use for a period of up to between six and ten hours, e.g., approximately 8 hours. For some applications, a water trap as described herein is configured for use for a shorter time period (e.g., a time period of between one hour and five hours, e.g., approximately two hours). For some such applications, the inlet and outlet portions of water trap 28 are shaped such that the length of the internal hollow volume defined by the tube through which the respiratory gases flow is more than 20 mm, and/or less than 50 mm, e.g., between 20 mm and 50 mm. For some such applications, the volume of the internal hollow volume defined by the tube through which the respiratory gases flow is more than 0.02 cc and/or less than 0.04 cc, e.g., between 0.02 cc and 0.04 cc. For some such applications, the ratio between the internal hollow volume defined by the inlet portion and the internal hollow volume defined by the outlet portion is more than 1:1 and/or less than 2:1, e.g., between 1:1 and 2:1

Figures 4A, 4B, 4C:
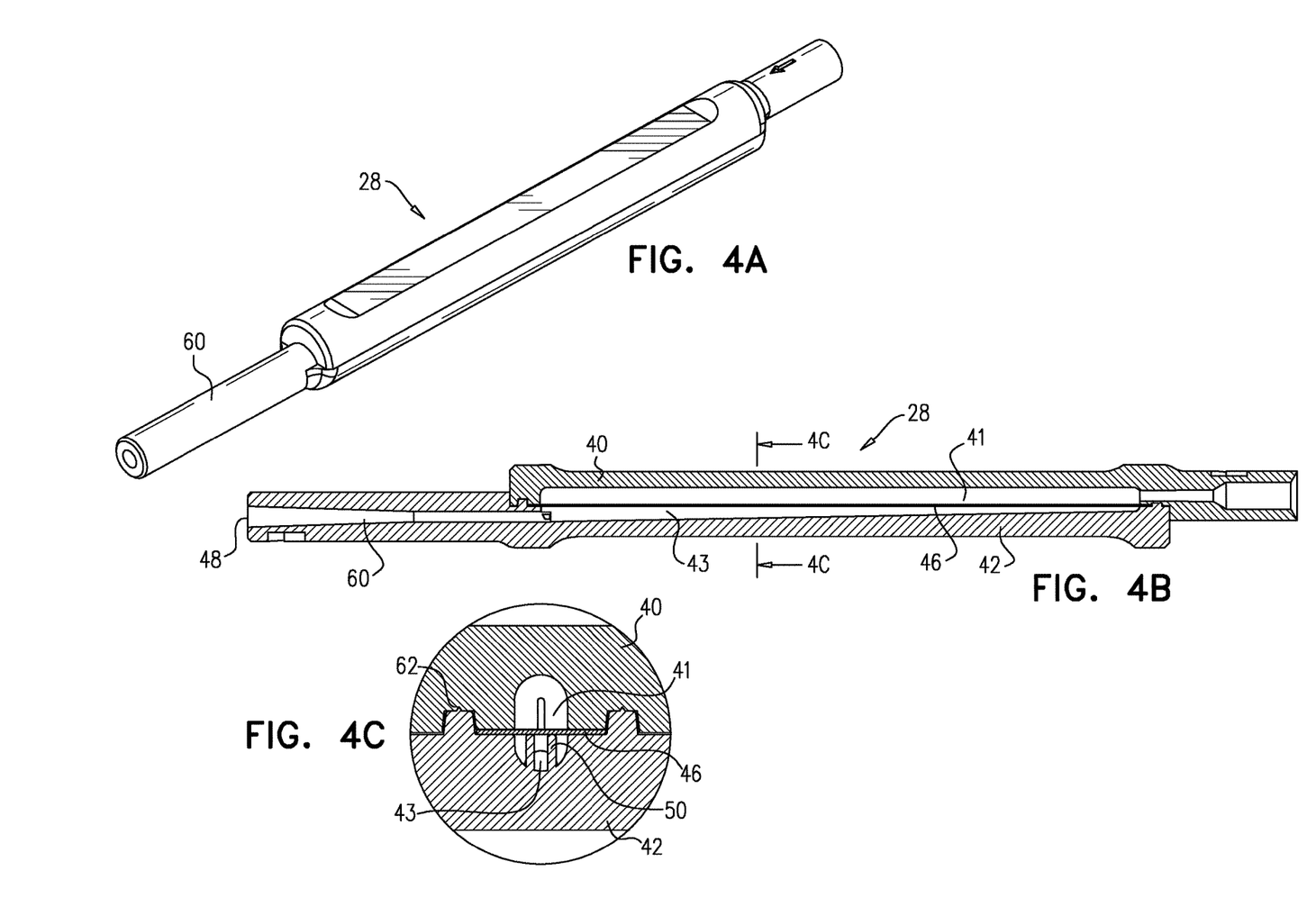
FIGS. 4A, 4B, and 4C are schematic illustrations of respective views of the water trap, in accordance with some applications of the present invention.

Reference is now made to FIGS. 4A, 4B, and 4C, which are schematic illustrations of respective views of water trap 28, in accordance with some applications of the present invention. FIG. 4A shows a three-dimensional external view of the water trap, and FIGS. 4B and 4C show respective cross-sectional views of the water trap. Water trap 28 as shown in FIGS. 4A, 4B, and 4C is generally similar to water trap 28 as shown in FIGS. 2A, 2B, 3A, and 3B, except for the differences described hereinbelow.

As described hereinabove, filtered gas typically flows from outlet portion 42 to sensing chamber 24. For some applications, the outlet portion defines an extended male fitting 60 of a Luer lock that is configured to become coupled to a corresponding, female portion (not shown). For some applications, the corresponding female portion is an intermediate Luer portion that is couplable to the sensing chamber of the capnometer. For some applications (shown in FIGS. 6A-B), the outlet portion includes a Luer component 80 (or another coupling portion) that is directly couplable to the sensing chamber of the capnometer.

With reference to FIG. 4B, for some applications, internal hollow volume 43 defined by outlet portion 42 diverges along the length of the outlet portion in the direction away from the inlet hole and toward the outlet hole. For some application, the divergence of the internal hollow volume defined by the outlet portion directs gas flow toward outlet hole 48.

With reference to FIG. 4C, for some applications, the inlet portion and outlet portion define an interface 62 that is configured to facilitate coupling of the portions to each other via ultrasonic welding. For example, as shown, the inlet portion and outlet portion may define interlocking male and female portions having triangular cross-sectional shapes.

Figure 5A:
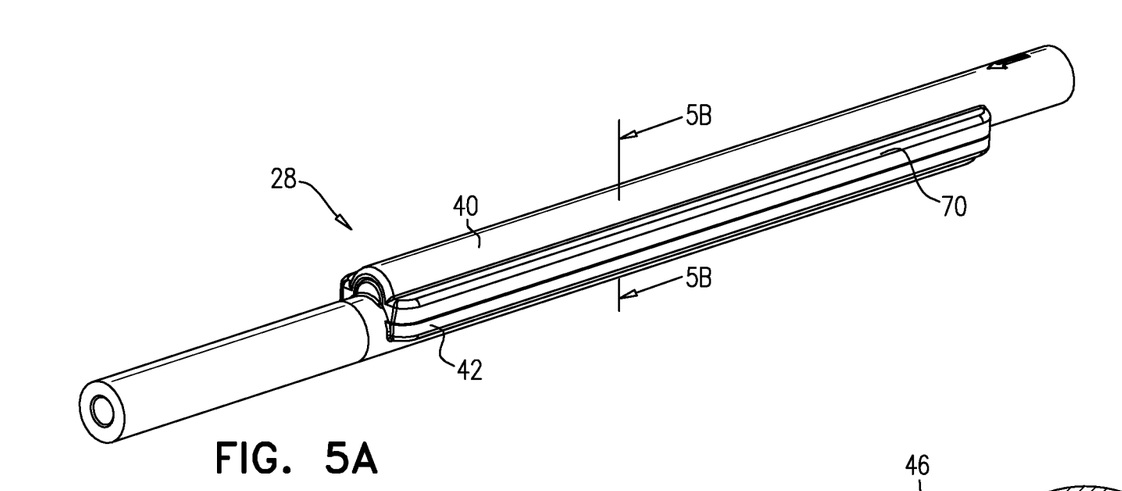
FIGS. 5A and 5B are schematic illustrations of respective views of the water trap, in accordance with some applications of the present invention.
Figure 5B:
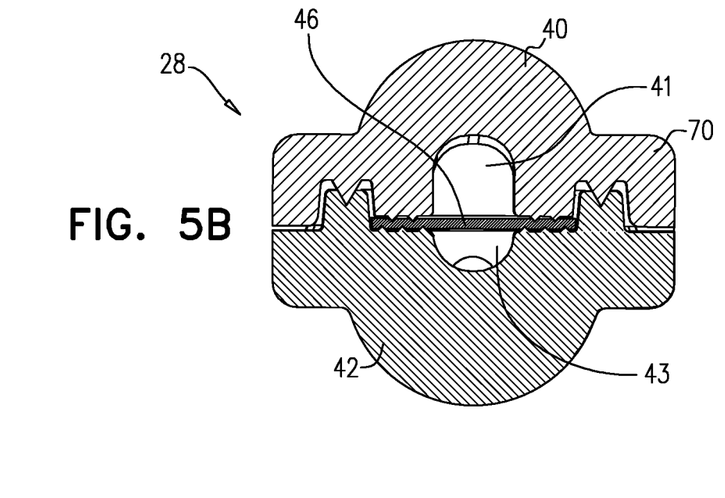

Reference is now made to FIGS. 5A and 5B, which are schematic illustrations of respective views of water trap 28, in accordance with some applications of the present invention. FIG. 5A shows a three-dimensional external view of the water trap, and FIG. 5B shows a cross-sectional view of the water trap. Water trap 28 as shown in FIGS. 5A and 5B is generally similar to water trap 28 as shown in other figures, except for the differences described hereinbelow.

For some applications, the external shape of the filter is different to that illustrated in FIG. 2A, for example. For example, for some applications, the water trap defines lateral projections 70, as shown in FIGS. 5A-B.

As described hereinabove, for some applications, outlet portion 42 defines one or more internal protruding portions, which may be shaped in a grid, or as a grill (i.e., in a plurality of parallel lines). Alternatively, as shown in FIG. 5B, the outlet portion does not define internal protruding portions. Typically, for applications in which the outlet portion does not define internal protruding portions, the ratio between the internal hollow volume of the inlet portion (i.e., the volume of the internal hollow volume defined by the inlet portion) and the internal hollow volume of the outlet portion (i.e., the volume of the internal hollow volume defined by the outlet portion) is between 2:1 and 4:1, as described hereinabove.

Figure 6A:
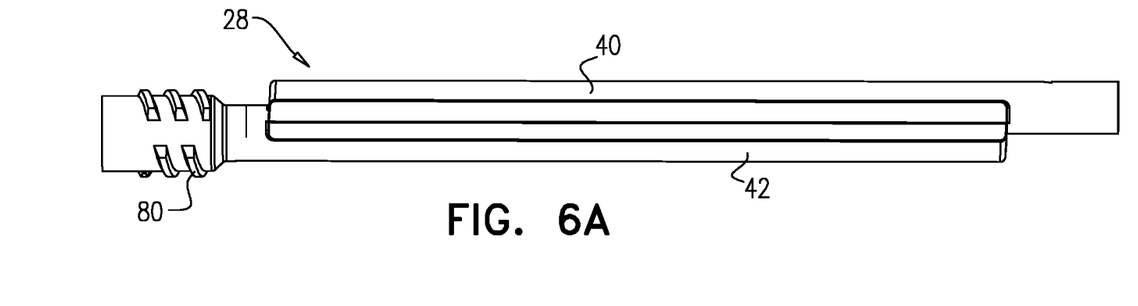
FIGS. 6A and 6B are schematic illustrations of respective views of, respectively, the water trap and an outlet portion of the water trap, in accordance with some applications of the present invention.
Figure 6B:
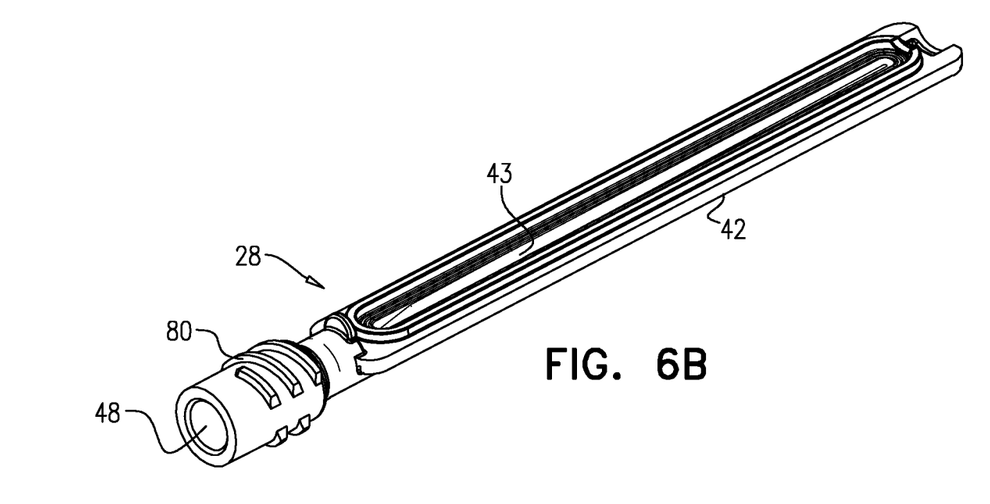

Reference is now made to FIGS. 6A and 6B, which are schematic illustrations of, respectively, water trap 28, and outlet portion 42 of the water trap, in accordance with some applications of the present invention. Water trap 28 as shown in FIGS. 6A and 6B is generally similar to water trap 28 as shown in other figures, except for the differences described hereinbelow.

As described hereinabove, and as shown in FIGS. 6A and 6B, for some applications, outlet portion 42 includes a Luer component 80 (or another coupling portion) that is directly couplable to the sensing chamber of the capnometer. For such applications, outlet hole 48 is typically defined by the Luer component, as shown.

As described hereinabove, in accordance with respective applications, outlet portion 42 defines one or more internal protruding portions, or does not define one or more internal protruding portions. (Irrespective of whether the outlet portion defines internal protruding portions, the ratio between the internal hollow volume defined by the inlet portion (i.e., the volume of internal hollow volume 41 defined by the inlet portion) and the internal hollow volume defined by the outlet portion (i.e., the volume of internal hollow volume 43 defined by the outlet portion) is typically between 2:1 and 4:1.) In accordance with respective applications, the outlet portion includes an extended male fitting of a Luer lock, includes a Luer component 80 (or another coupling portion) that is directly couplable to the sensing chamber of the capnometer, or does not include either of these features. The scope of the present invention includes a water trap that combines any combination of the above-described features.

Although some applications of the present invention have been described as using water trap 28 to filter respiratory gases in the context of capnography, the scope of the present invention includes using a water trap as described herein in any relevant setting, mutatis mutandis. For example, the scope of the present invention includes using water trap 28 in other medical settings, and/or in industrial settings. Similarly, although some applications of the present invention have been described as using the trap to trap water, for some applications, trap 28 is used to trap other elements, such as microorganisms (e.g. bacteria), mutatis mutandis. Typically, membrane filter 46 is selected such as to trap the elements within inlet portion 40, in accordance with the techniques described herein. In accordance with some applications, a trap as generally described herein is used in a transducer protector, an intravenous (IV) filter, an insufflation filter, an epidural filter, etc., mutatis mutandis. For some applications, the trap acts as a gas filter, and in some application, the trap acts as a fluid filter, mutatis mutandis. For some applications, the filter is hydrophobic.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus comprising:
a water trap comprising:
an inlet portion, via which a mixture of gas and water is configured to enter the water trap;
an outlet portion, via which the gas is configured to exit the water trap, the inlet portion and the outlet portion being formed separately from one another and being coupled to one another, such as to form a tube that defines a longitudinal axis and that defines an internal hollow volume through which the gas is configured to flow; and
a membrane filter disposed in a flat configuration within the tube, between the inlet portion and the outlet portion, such that gas passes through the membrane filter from the inlet portion to the outlet portion by travelling in a direction that is perpendicular to the longitudinal axis of the tube, the membrane filter being configured to prevent the water from passing therethrough,
the water trap being configured to retain the water that is prevented from passing through the membrane filter within the inlet portion.

2. The apparatus according to claim 1, wherein the water trap does not include a reservoir that is separated from the inlet portion by a channel and into which water that is prevented from passing through the membrane filter is transferred.

3. The apparatus according to claim 1, wherein the water trap does not include a channel via which to transfer water that is prevented from passing through the membrane filter out of the inlet portion.

4. The apparatus according to claim 1, wherein the water trap is configured to be used with a capnometer that includes a sensing chamber, and the water trap is configured to prevent water from entering the sensing chamber.

5. The apparatus according to claim 1, wherein a length of the internal hollow volume defined by the tube formed by the inlet portion and the outlet portion is between 30 mm and 150 mm.

6. The apparatus according to claim 1, wherein a length of the internal hollow volume defined by the tube formed by the inlet portion and the outlet portion is between 20 mm and 50 mm.

7. The apparatus according to claim 1, wherein a volume of the internal hollow volume defined by the tube formed by the inlet portion and the outlet portion is between 0.05 cc and 0.3 cc.

8. The apparatus according to claim 1, wherein a volume of the internal hollow volume defined by the tube formed by the inlet portion and the outlet portion is between 0.02 cc and 0.04 cc.

9. The apparatus according to claim 1, wherein a ratio between an internal hollow volume defined by the inlet portion and an internal hollow volume defined by the outlet portion is between 2:1 and 4:1.

10. The apparatus according to claim 1, wherein a ratio between an internal hollow volume defined by the inlet portion and an internal hollow volume defined by the outlet portion is between 1:1 and 2:1.

11. The apparatus according to claim 1, wherein the water trap is configured such that a T90 rise time of respiratory gases through the water trap at a flow of 50 cc/min is less than 200 ms, when the water trap is in a standalone configuration.

12. The apparatus according to claim 1, wherein the membrane filter is configured to substantially maintain laminar flow of gas that passes through the water trap.

13. The apparatus according to claim 1, wherein the water trap is configured such that a pressure drop of gas that passes through the water trap at a flow of 50 cc/min is less than 20 mBar.

14. The apparatus according to claim 1, wherein the membrane filter comprises a polymer selected from the group consisting of: expanded polytetrafluoroethylene (EPTFE), polytetrafluoroethylene (PTFE), a polyolefin, glass micro-fiber, polyethersulfone (PES), polypropylene (PP), and polyvinylidene fluoride (PVDF).

15. The apparatus according to claim 1, wherein the membrane filter comprises a membrane filter having a pore size of between 0.1 microns and 10 microns.

16. The apparatus according to claim 1, wherein the outlet portion is shaped to define one or more internal protruding portions that protrude from an inner surface of the outlet portion.

17. The apparatus according to claim 16, wherein the one or more internal protruding portions that protrude from the inner surface of the outlet portion maintain the membrane filter parallel to the longitudinal axis of the tube defined by the inlet and outlet portions.

18. A method comprising:
manufacturing a water trap by:
providing an inlet portion;
providing an outlet portion;
placing a membrane filter in a flat configuration between the inlet portion and the outlet portion, the membrane filter being configured to prevent water from passing therethrough; and
while the membrane filter is disposed between the inlet portion and the outlet portion coupling the inlet portion and the outlet portion to one another, such that inlet portion and the outlet portion define a tube that defines a longitudinal axis and that defines an internal hollow volume, and gas passes through the membrane filter from the inlet portion to the outlet portion by travelling in a direction that is perpendicular to the longitudinal axis of the tube,
without attaching a reservoir to the water trap into which to transfer water that is prevented from passing through the membrane filter.

19. A method for use with a sensing unit of a capnometer, the method comprising:
providing a water trap that includes:
an inlet portion and an outlet portion, the inlet portion and the outlet portion being coupled to one another, such as to form a tube that define a longitudinal axis and that defines an internal hollow volume, and
a membrane filter disposed in a flat configuration within the tube, between the inlet portion and the outlet portion, such that gas passes through the membrane filter from the inlet portion to the outlet portion by travelling in a direction that is perpendicular to the longitudinal axis of the tube; and
placing the water trap in fluid communication with respiratory gases and water exhaled by a subject, and the sensing unit of the capnometer such that:
the respiratory gases and water enter the water trap via the inlet portion,
the water trap prevents water from entering the sensing unit of the capnometer, by the membrane filter preventing the water from passing therethrough, such that the water that is prevented from passing through the membrane filter is retained within the inlet portion, and
the respiratory gases flow through the membrane filter and out of the outlet portion to the sensing unit of the capnometer.

* * * * *